(12) United States Patent
Rogers et al.

(10) Patent No.: US 6,471,675 B1
(45) Date of Patent: Oct. 29, 2002

(54) PASSIVE FLOW CONTROL DEVICES FOR IMPLANTABLE PUMPS

(75) Inventors: Charles Rogers, Maple Grove; Warren Starkebaum, Plymouth; Raymond McMullen, Shorewood, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/303,004

(22) Filed: Apr. 30, 1999

(51) Int. Cl.$^7$ .................................................. A61M 1/00
(52) U.S. Cl. ................... 604/151; 604/890.1; 604/892.1
(58) Field of Search ............................ 604/890.1–892.1, 604/93, 131, 151, 156, 246–249

(56) References Cited

U.S. PATENT DOCUMENTS

| | | | |
|---|---|---|---|
| 4,077,405 A | | 3/1978 | Haerten et al. |
| 4,193,397 A | | 3/1980 | Tucker et al. |
| 4,258,711 A | | 3/1981 | Tucker et al. |
| 4,838,887 A | * | 6/1989 | Idrisss |
| 5,049,141 A | | 9/1991 | Olive |
| 5,281,210 A | * | 1/1994 | Burke et al. .............. 604/891.1 |
| 5,464,392 A | | 11/1995 | Epstein et al. |
| 5,820,589 A | | 10/1998 | Torgerson et al. |
| 5,839,467 A | | 11/1998 | Saaski et al. |

FOREIGN PATENT DOCUMENTS

| | | |
|---|---|---|
| DE | 196 42 234 C1 | 4/1998 |
| EP | 0 134 614 A1 | 3/1985 |
| WO | WO 91/16091 A1 | 10/1991 |

* cited by examiner

*Primary Examiner*—Brian L. Casler
*Assistant Examiner*—Kevin C. Sirmons
(74) *Attorney, Agent, or Firm*—Banner & Witcoff, Ltd.

(57) ABSTRACT

An implantable drug delivery device is provided with a passive flow control device is provided in the form of a valve which may assume two flow states. Flow control is achieved by duty cycling the valve using a control module which generates appropriate signals in response to an input telemetry signal corresponding to a desired flow rate. In another embodiment, a passively controlled bolus delivery device is provided to deliver a bolus of drug in addition to normal dosage.

1 Claim, 3 Drawing Sheets

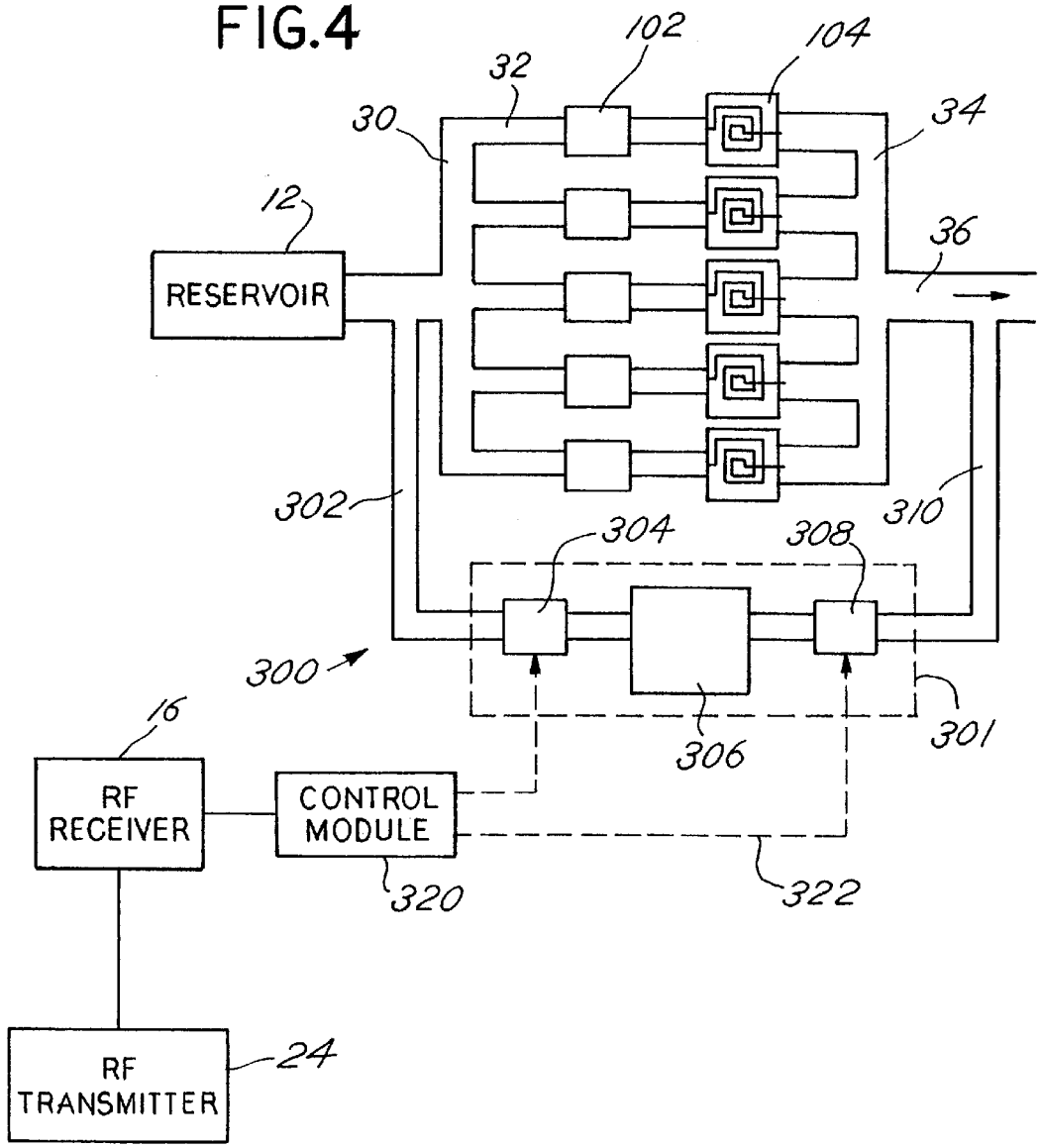

PASSIVE FLOW CONTROL DEVICES FOR IMPLANTABLE PUMPS

BACKGROUND OF THE INVENTION

1. Field of the Invention

The present invention relates to implantable apparatus for delivering beneficial agents, including drugs to a living body. More particularly, the present invention relates to implantable flow control devices for controlling delivery of beneficial agents to a living body.

2. Description of the Related Art

It is known to provide implanted drug infusion pumps to deliver a controlled, sustained dosage of beneficial agent or drug to the living human body. Such infusion pumps are generally classified as fixed rate infusion pumps or variable rate infusion pumps. Fixed rate infusion pumps deliver drug-carrying fluid at a preset flow rate, which cannot be changed after manufacture. Variable flow rate implantable pumps permit adjustment of the flow rate, but only prior to implantation. Readjustment of the flow rate of variable rate pumps requires removal of the pump from the patient's body and related surgery. Because of the surgical intrusiveness typically required for flow rate changes for both fixed rate and adjustable rate pumps, there has developed a trend towards selectable-rate pumps, which permit flow adjustment while the pump remains implanted in the living body.

Flow control in selectable rate pumps, however, is complicated by the need to limit or minimize the power consumption. To this end, there have been efforts to provide passive flow control elements on selectable rate pumps for minimizing power consumption while providing flow control.

For example, U.S. Pat. No. 5,820,589, to Torgerson and McMullen, the subject matter of which is incorporated herein, in its entirety, discloses the concept of an implantable pump, which is provided with a passive regulator in the form of a manifold communicating with a restrictor network, with a number (n) of bi-stable valves with two flow states, or a number (n) of multi-stable valves with a number (m) of flow states. With the bi-stable valve configuration, the combination overall allows for $2^n$ flow rate options. With the multi-stable valves, the system has $m^n$ flow rate options. Ideally, such bi-stable or multi-stable valves would have no requirement for power except during flow state changes. Power is typically provided via RF signal with suitable electronic implements provided on the pump for providing an induced voltage from the RF signal. While such known passive flow control systems provide variability in flow rates, the number of attainable flow configurations is somewhat limited. It would therefore be desirable to provide an implantable pump with a passive flow control system which provides increased adjustability in flow rates over known systems.

In drug infusion applications, it is frequently desirable to provide for the introduction of a drug bolus to the patient. Bolus dosage may be required, for example, when a patient's activity results in increased pain that is not adequately controlled with normal dosage. Known passive control systems do not provide for the administering of a drug bolus. Thus, there is a need to provide an implantable pump with a passive flow control system which permits the metering and delivery of a bolus of drug.

SUMMARY OF THE INVENTION

The present invention solves the aforementioned problems and others by providing an implantable drug infusion pump with a passive flow control device with increased variability in flow settings over heretofore known devices. In a preferred embodiment, the invention provides a bi-stable valve which is duty-cycled by a control module to achieve a desired average flow rate over time. The control module provides appropriate signals at appropriate times to open and close the valve to achieve a desired average flow rate over time. A flow restrictor may be provided downstream of the valve as a safety feature to limit flow or to achieve a desired flow rate range.

The invention also provides a drug infusion pump with a passive flow control device which provides for metering and delivery of a bolus of drug. In a preferred embodiment, a flow conduit communicates with the pressurized reservoir and with a first normally closed, bi-stable valve. The first bi-stable valve is in fluid communication with an accumulator for accumulating a bolus of drug. A second bi-stable valve isolates the drug supply stored in the accumulator from a drug delivery catheter. To meter a drug bolus into the accumulator, a control module provides an appropriate signal to open and close the first valve and permit ingress of a desired amount of drug to the accumulator. The inlet valve is closed after the bolus has accumulated. When a bolus delivery is desired, the control module delivers appropriate signals to the second valve to release the bolus from the accumulator.

BRIEF DESCRIPTION OF THE DRAWINGS

The invention will be described with reference to the drawings, which form a part of this specification. Those of ordinary skill will understand that the invention is not intended to be limited to these exemplary embodiments illustrated in the drawings, of which:

FIG. 4 is a diagrammatic illustration of a fluid control system and bolus delivery device according to another preferred embodiment of the invention.

DETAILED DESCRIPTION OF THE INVENTION

Figure 1:
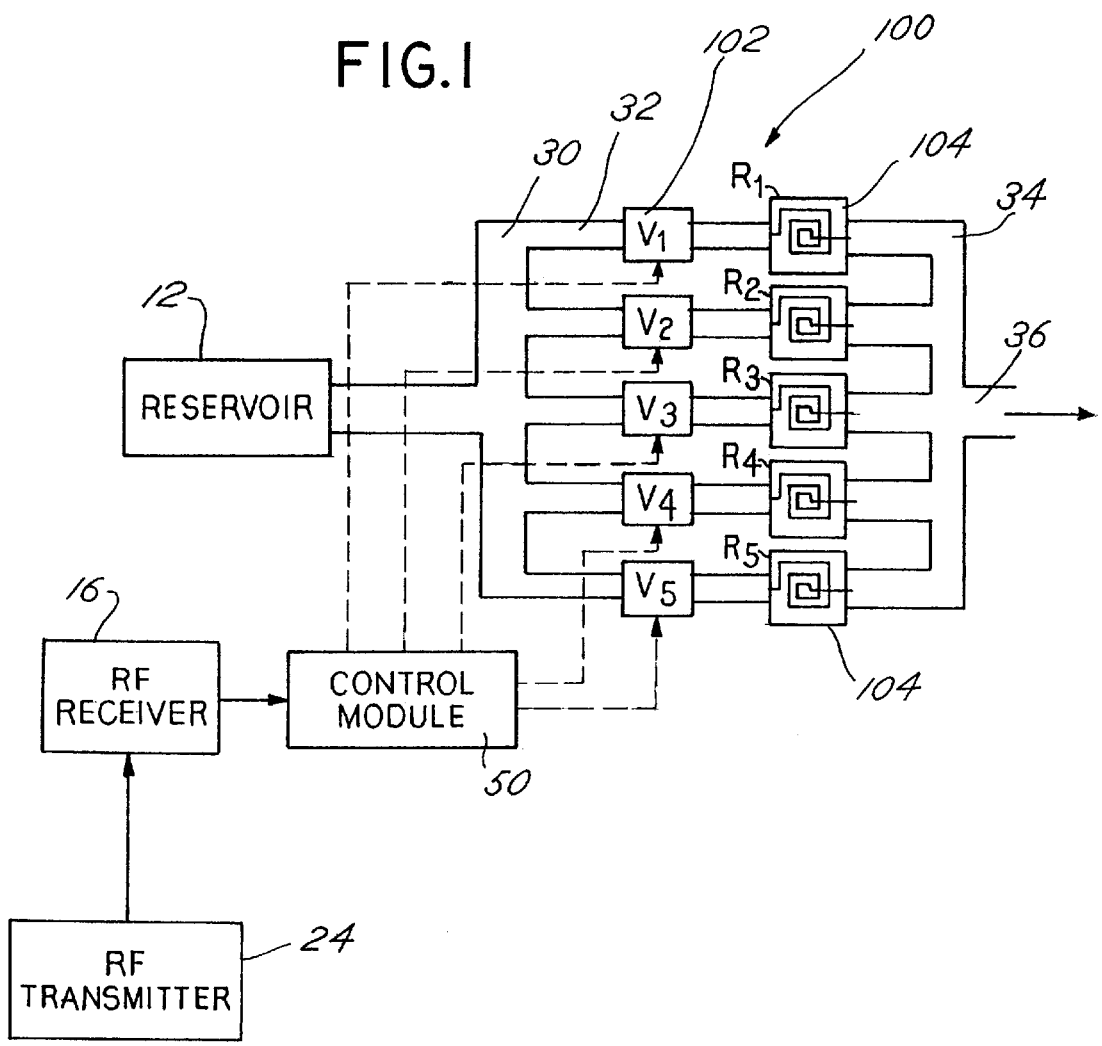
FIG. 1 is a diagrammatic illustration of a fluid control system according to a preferred embodiment of the invention.

FIG. 1 illustrates diagrammatically the components of an implantable pump incorporating a passive flow control device 100 according to a preferred embodiment of the present invention. A pressurized reservoir 12 is provided with beneficial agent in a carrier fluid and communicates with an inlet manifold 30 for conveying fluid to a plurality of inlet branches 32 and a like plurality of valves 102. While five valves are represented in FIG. 1, it will be understood by those of ordinary skill that any number of valves may be provided to achieve a desired range of flow rates. Associated with each valve is a fluid restrictor 104, which is designed to provide a predetermined flow rate, usually proportional to the pressure differential across the restrictor 104. In fluid communication with each restrictor is an outlet manifold 34 which collects the fluid flow exiting each restrictor 104 and conveys the cumulative flow through a delivery conduit 36 to a catheter (not shown) for delivery to a desired location within the body.

In accordance with the invention, each valve V1–V5 is provided with a respective control signal along a signal path from the control module 50. Consistent with known telemetry techniques, control module 50, in conjunction with radio frequency (RF) receiver 16, provides power, in the form of a voltage signal to the respective valves V1–V5. The voltage signals are preferably in the form of impulses of sufficient duration and magnitude to change the state of the valves V1–V5. Control module 50 thus generates respective signals to each of valves V1–V5, based on signals received from RF receiver 16 corresponding to a particular desired one of the available flow rate settings.

In accordance with the invention, the respective flow rates for restrictors R1–R5 are selected to provide a desired range of flows. Typically, a flow rate range between 10 and 2000 μL/day (microliters per day) are practical for most drug administering applications. Preferably, the flow rates of restrictors R1–R5 are related to provide a uniform interval of flow rate increase or decrease for changed states of valves V1–V5. For example, each restrictor may be adapted to provide twice the flow rate of the adjacent and lower flowing restrictor: restrictor R1 may be adapted to provide a flow rate of 10 μL/day, restrictor R2 a flow rate of 20 μL/day, restrictor R3 a flow rate of 40 μL/day, restrictor R4 a flow rate of 80 μL/day and restrictor R5 a flow rate of 160 μL/day. range of 10 to 2000 μL/day, with adjustment intervals of 10 μL/day, eight restrictors and corresponding bi-stable valves would be required.

As will be appreciated by those of ordinary skill, the valves 102 of flow control device 100 may be implemented in micromachinery as detailed, for example, in U.S. Pat. No. 5,839,467 to Saaski et al, the subject matter of which is incorporated herein by reference in its entirety. Similarly, restrictors 104 may be provided as micromachined elements or capillary tubes, for example. Alternatively, valves 102 may be macromachined bi-stable elements, including but not limited to solenoid valves, piezoelectric operated valves, or shape memory alloy actuated valves incorporating NITONOL, for example.

Figure 2:
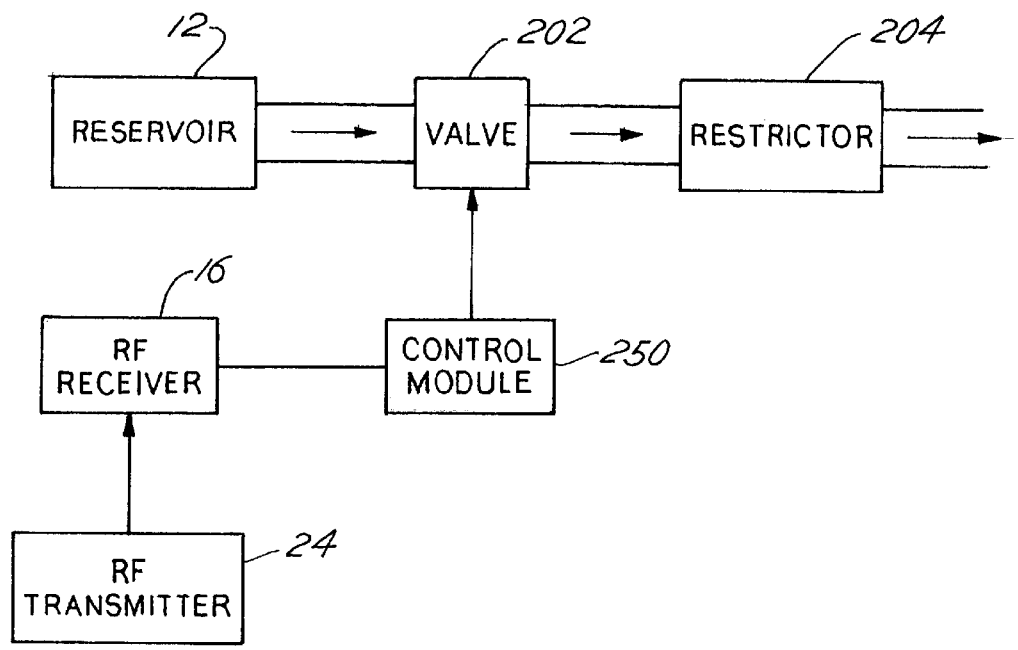
FIG. 2 is a diagrammatic illustration of a fluid control system according to another preferred embodiment of the invention.
Figure 3:
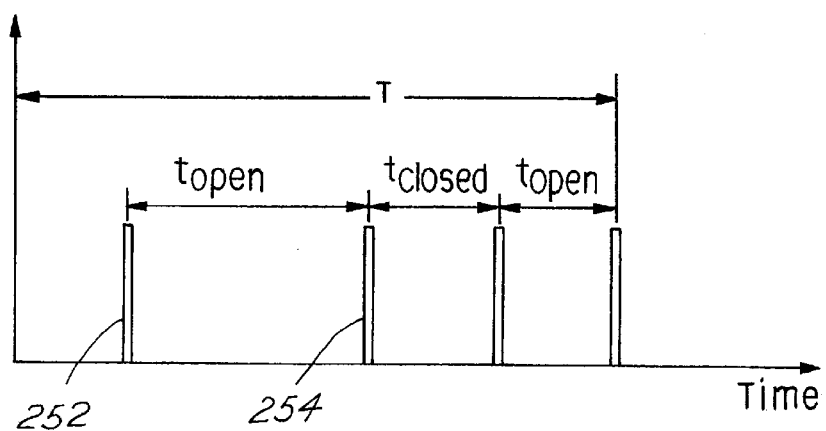
FIG. 3, is a graph of a duty cycling signal associated with the embodiment of FIG. 2.

Referring now to FIGS. 2 and 3, in accordance with another aspect of the invention, a passive flow control device provides for duty cycling a valve 202 to achieve a desired flow rate. Control module 250 is adapted to provides intermittent signals to change to state of valve 202 to achieve desired time-average flow rates. Valve 202 may be a micromachined bi-stable valve as described above with reference to FIG. 1. Valve 202 is capable of being configured to one of two states by an appropriate electrical signal. These two states may correspond to an "open" and "closed" condition, or may correspond to two different flow rates. A flow restrictor 204 may be provided to reduce the flow through valve 202.

In accordance with the present invention, control module 250 provides signals to periodically change the state of valve 202 to achieve a desired flow rate. Referring to FIG. 3, a first signal 252 is provided from control module 250 to change the state of the bi-stable valve to an open-state. For a time period, $t_{open}$, the valve 202 remains open and fluid is permitted to pass at a predetermined rate to the patient's body. Then, after $t_{open}$ has expired, a second signal 254 is sent by control module 250 to change the state of the bi-stable valve 202 to a closed-state, in which the valve 250 will remain for a period $t_{closed}$. In accordance with the invention, the duration of the open and closed states of valve 202 are chosen to achieve a desired average flow rate over a large time interval, T. The flow restrictor 204 may be employed to reduce the flow through valve 202, to thereby provide for more accurate control of the flow rate when the time intervals $t_{open}$ and $t_{closed}$ would otherwise be too small to be accurately controlled by signals from control module 250.

Those of ordinary skill will recognize that a virtually infinite number of average flow rates may be selected by appropriate selection of the duration of time that the valve 202 remains in each of the two states. It will be appreciated that the duty cycling described with respect to FIGS. 2 and 3 may be used in conjunction with a number of valves in a flow control network such as that described above with respect to FIG. 1 while still falling within the scope of the invention described herein.

Referring now to FIG. 4, another aspect of the invention provides a passive flow control system 300 for metering and delivering a drug bolus. In addition to the flow control network described above with respect to FIG. 1, a bolus delivery component 301 in fluid communication with reservoir 12 may be employed to meter and deliver a bolus of drugs. An inlet passage 302 is provided to direct flow of drug-carrying fluid from the reservoir 12 to an inlet valve 304. An accumulator 306 is in fluid communication with an outlet end of inlet valve 304 to permit the ingress of fluid. An outlet valve 308, is provided at an outlet end of accumulator 306. Inlet valve 304 and outlet valve 308 may be bi-stable valves adapted to remain in their closed positions in the absence of a signal from control module 320.

In operation, upon appropriate telemetry to RF receiver 16 indicating that an operator, or the patient, has requested a bolus of drug, control module 320 provides a first signal to inlet valve 304 to maintain inlet valve 304 in an open state for a predetermined time, corresponding to the amount of drug to be included in the bolus. Under pressure from reservoir 12, drug flows into accumulator. When the predetermined period of time has expired, inlet valve 304 closes. Subsequently, control module 320 initiates a control signal to outlet valve 308 and holds outlet valve 308 in an open state to permit the bolus of drug, which is pressurized within the accumulator, to be delivered to the outlet conduit 310.

Although the preferred embodiment of this invention has been described above in some detail, it should be appreciated that a variety of embodiments will be readily apparent from the foregoing description to persons of ordinary skill. The description is intended to be illustrative of the preferred embodiment of this invention and not intended to be limiting to the scope of protection sought by the applicants, which scope is defined by the appended claims.

What is claimed is:

1. A method of controlling flow in an implantable drug delivery device comprising the steps of:

a) providing a bi-stable flow control element;

b) providing a control module for generating a signal to the flow control element;

c) duty cycling the flow control element to obtain a desired average flow rate over time;

d) providing a bolus delivery component in parallel communication with the flow control element; and e) controlling operation of the bolus delivery component to permit accumulation of a predetermined amount of drug bolus in the bolus delivery device and subsequent release of the accumulated bolus.

\* \* \* \* \*